(12) United States Patent
Benkowsi et al.

(10) Patent No.: US 8,376,926 B2
(45) Date of Patent: Feb. 19, 2013

(54) ROTARY BLOOD PUMP

(75) Inventors: Robert J. Benkowsi, Houston, TX (US); Lee Hudson, Houston, TX (US)

(73) Assignee: MicroMed Technology, Inc., Houston, TX (US)

( * ) Notice: Subject to any disclaimer, the term of this patent is extended or adjusted under 35 U.S.C. 154(b) by 493 days.

(21) Appl. No.: 12/323,063

(22) Filed: Nov. 25, 2008

(65) Prior Publication Data

US 2009/0143635 A1 Jun. 4, 2009

Related U.S. Application Data

(60) Provisional application No. 60/991,212, filed on Nov. 29, 2007.

(51) Int. Cl.
*A61N 1/32* (2006.01)
*A61M 1/10* (2006.01)
*F04B 35/00* (2006.01)

(52) U.S. Cl. ............... 600/16; 623/3.14; 417/355
(58) Field of Classification Search .......... 600/16; 623/3.14; 417/355
See application file for complete search history.

(56) References Cited

U.S. PATENT DOCUMENTS

| | | | |
|---|---|---|---|
| 5,527,159 A | 6/1996 | Bozeman, Jr. et al. | |
| 5,947,892 A * | 9/1999 | Benkowski et al. ............ | 600/16 |
| 6,183,412 B1 | 2/2001 | Benkowski et al. | |
| 7,175,588 B2 | 2/2007 | Morello | |
| 7,229,258 B2 * | 6/2007 | Wood et al. .................... | 417/355 |
| 7,396,327 B2 | 7/2008 | Morello | |
| 2004/0215050 A1 | 10/2004 | Morello | |
| 2005/0004418 A1 | 1/2005 | Morello | |
| 2005/0107657 A1 | 5/2005 | Carrier et al. | |
| 2005/0131271 A1 | 6/2005 | Benkowski et al. | |
| 2005/0135942 A1 | 6/2005 | Wood et al. | |
| 2005/0250975 A1 | 11/2005 | Carrier et al. | |
| 2005/0250976 A1 | 11/2005 | Melvin et al. | |
| 2006/0241335 A1 | 10/2006 | Benkowski et al. | |
| 2007/0004959 A1 | 1/2007 | Carrier et al. | |
| 2007/0100196 A1 | 5/2007 | LaRose et al. | |
| 2008/0281146 A1 | 11/2008 | Morello | |
| 2009/0005632 A1 | 1/2009 | Schima et al. | |

OTHER PUBLICATIONS

International Search Report for Corresponding International Patent Application No. PCT/US2008/084779.
Written Opinion for Corresponding International Patent Application No. PCT/US2008/084779.

* cited by examiner

*Primary Examiner* — Nicole F Lavert
(74) *Attorney, Agent, or Firm* — Sutton McAughan Deaver PLLC

(57) ABSTRACT

A blood pump consisting of an inflow cannula, a stator fixed to the pump housing, a flow straightener, an impeller, and a diffuser. The pump may include a flow straightener assembly consisting of the flow straightener body and front shaft. The pump may include an impeller assembly with a bearing on the front hub section. The pump may have a body contour which is shaped such that the rear section of the flow straightener body blends into the inserted shaft and there is no axial gap between the end of the flow straightener other than the ends of the blades and the front hub of the impeller.

15 Claims, 3 Drawing Sheets

ROTARY BLOOD PUMP

CROSS REFERENCE TO RELATED APPLICATIONS

This application claims the benefit of and priority to U.S. Provisional Patent Application No. 60/991,212, filed on Nov. 29, 2007, the entire disclosure of which is incorporated by reference.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

1. Field of the Invention

The inventions disclosed and taught herein relate generally to implantable blood pumps; and more specifically related to implantable left ventricular assist devices and methods of use.

2. Description of the Related Art.

U.S. Pat. No. 5,527,159 entitled "Rotary Blood Pump" discloses "A rotary blood pump includes a pump housing for receiving a flow straightener, a rotor mounted on rotor bearings and having an inducer portion and an impeller portion, and a diffuser. The entrance angle, outlet angle, axial and radial clearances of blades associated with the flow straightener, inducer portion, impeller portion and diffuser are optimized to minimize hemolysis while maintaining pump efficiency. The rotor bearing includes a bearing chamber that is filled with cross-linked blood or other bio-compatible material. A back emf integrated circuit regulates rotor operation and a microcomputer may be used to control one or more back emf integrated circuits. A plurality of magnets are disposed in each of a plurality of impeller blades with a small air gap. A stator may be axially adjusted on the pump housing to absorb bearing load and maximize pump efficiency."

The inventions disclosed and taught herein are directed to an improved implantable axial blood pump.

BRIEF SUMMARY OF THE INVENTION

A blood pump consisting of an inflow cannula, a stator fixed to the pump housing, a flow straightener, an impeller, and a diffuser. The pump may include a flow straightener assembly consisting of the flow straightener body and front shaft. The pump may include an impeller assembly with a bearing on the front hub section. The pump may have a body contour which is shaped such that the rear section of the flow straightener body blends into the inserted shaft and there is no axial gap between the end of the flow straightener other than the ends of the blades and the front hub of the impeller.

DETAILED DESCRIPTION

Figure 1:
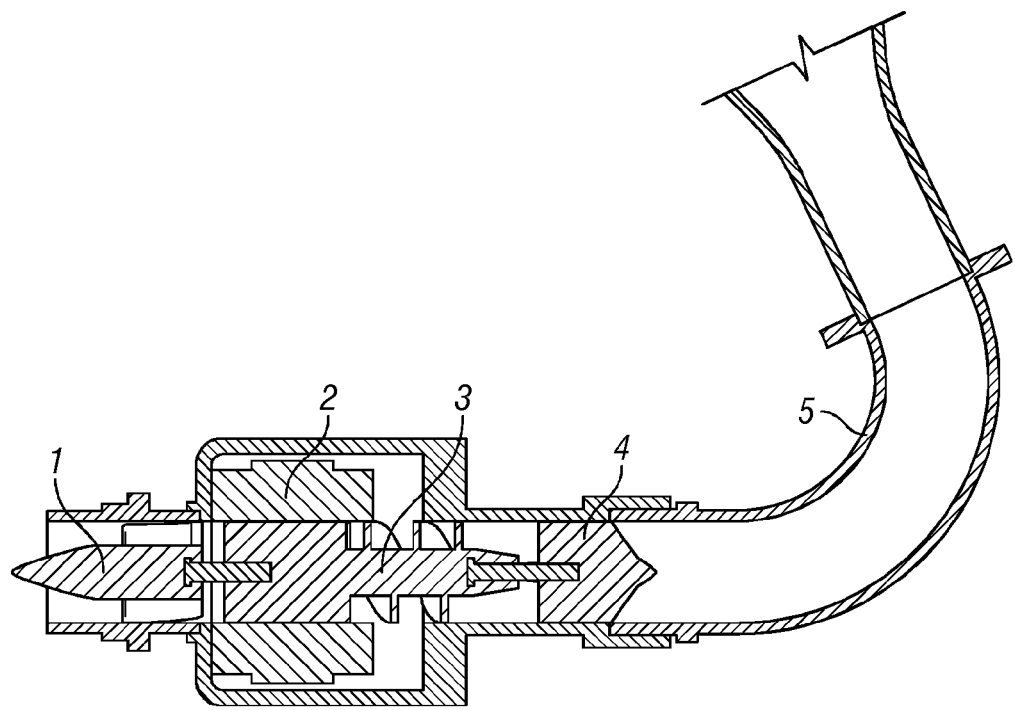
FIG. 1 illustrates a cross-section of a rotary blood pump.

The Figures described above and the written description of specific structures and functions below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time consuming in an absolute sense, such efforts would be, nevertheless, a routine undertaking for those of skill this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

Particular embodiments of the invention may be described below with reference to block diagrams and/or operational illustrations of methods. It will be understood that each block of the block diagrams and/or operational illustrations, and combinations of blocks in the block diagrams and/or operational illustrations, can be implemented by analog and/or digital hardware, and/or computer program instructions. Such computer program instructions may be provided to a processor of a general-purpose computer, special purpose computer, ASIC, and/or other programmable data processing system. The executed instructions may create structures and functions for implementing the actions specified in the block diagrams and/or operational illustrations. In some alternate implementations, the functions/actions/structures noted in the figures may occur out of the order noted in the block diagrams and/or operational illustrations. For example, two operations shown as occurring in succession, in fact, may be executed substantially concurrently or the operations may be executed in the reverse order, depending upon the functionality/acts/structure involved.

Computer programs for use with or by the embodiments disclosed herein may be written in an object oriented programming language, conventional procedural programming language, or lower-level code, such as assembly language and/or microcode. The program may be executed entirely on a single processor and/or across multiple processors, as a stand-alone software package or as part of another software package.

For all purposes of this disclosure, the entire subject matter of the following published applications and patents are incorporated by reference as if fully reprinted herein: U.S. Pat.

Nos. 5,527,159; 5,947,892; 6,183,412; 7,175,588; 7,396,327; pending U.S. patent application Ser. No. 10/501,112; and pending U.S. patent application Ser. No. 10/560,289.

An implantable axial flow blood pump may be designed to minimize the potential for thrombus formation in the area between the flow straightener and the front section of the impeller. The blood pump (Figure may comprise an inflow cannula (5), a flow straightener (4), an impeller (3), stator (4), and a diffuser (I).

Figure 2:
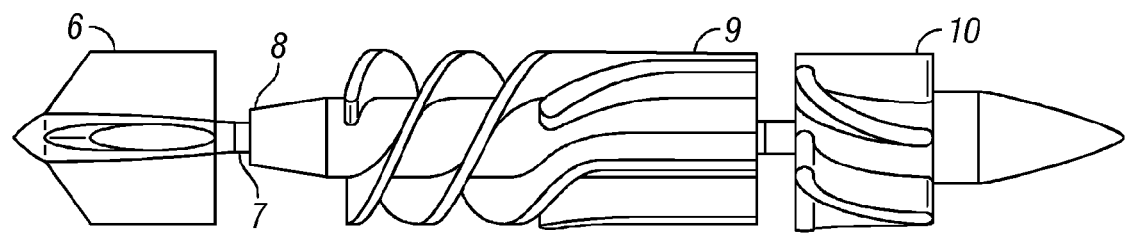
FIG. 2 illustrates and exploded view of a rotary blood pump.

FIG. 2 details the flow straightener (6), front shaft (7), front hub section of the impeller (8), impeller (9), and the diffuser (10). The flow straightener and impeller may be designed, and preferably are designed, to eliminate any area of blood or flow stagnation, such as near a stationary part. Blood flow direction is through the inflow cannula, through the flow straightener, impeller, and finally the diffuser.

Figure 3:
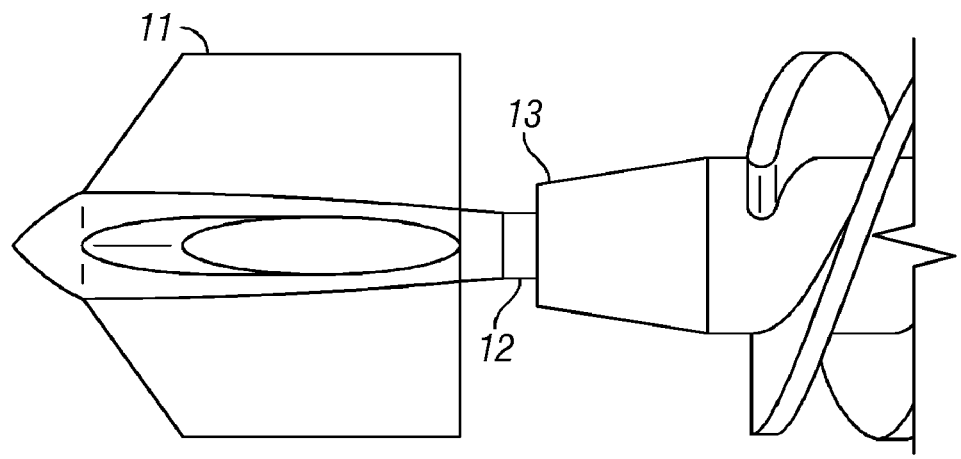
FIG. 3 illustrates a flow straightener assembly and front hub section.

FIG. 3 shows the flow straightener (11) with embedded front shaft (12) connecting with the front hub section of the impeller (13). By creating a body contour of the flow straightener that blends into the shaft little to no gap exists between the body of the flow straightener and the front hub of the impeller. This transition area minimizes or eliminates flow recirculation zones that contact stationary surfaces that could result in thrombus formation. Continual washing of surfaces, such as stationary surfaces, with flowing, non-stagnated flow lowers risk of thrombus formation.

Figure 4:
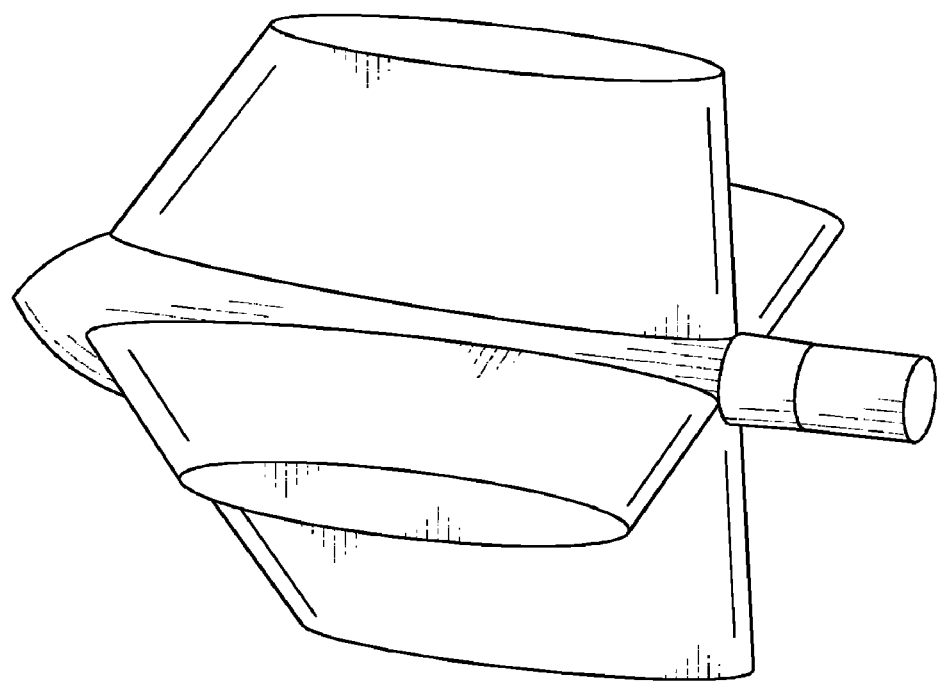
FIG. 4 illustrates a flow straightener assembly.

FIG. 4 shows the assembled flow straightener with contoured body which blends into the embedded front shaft.

Figure 5:
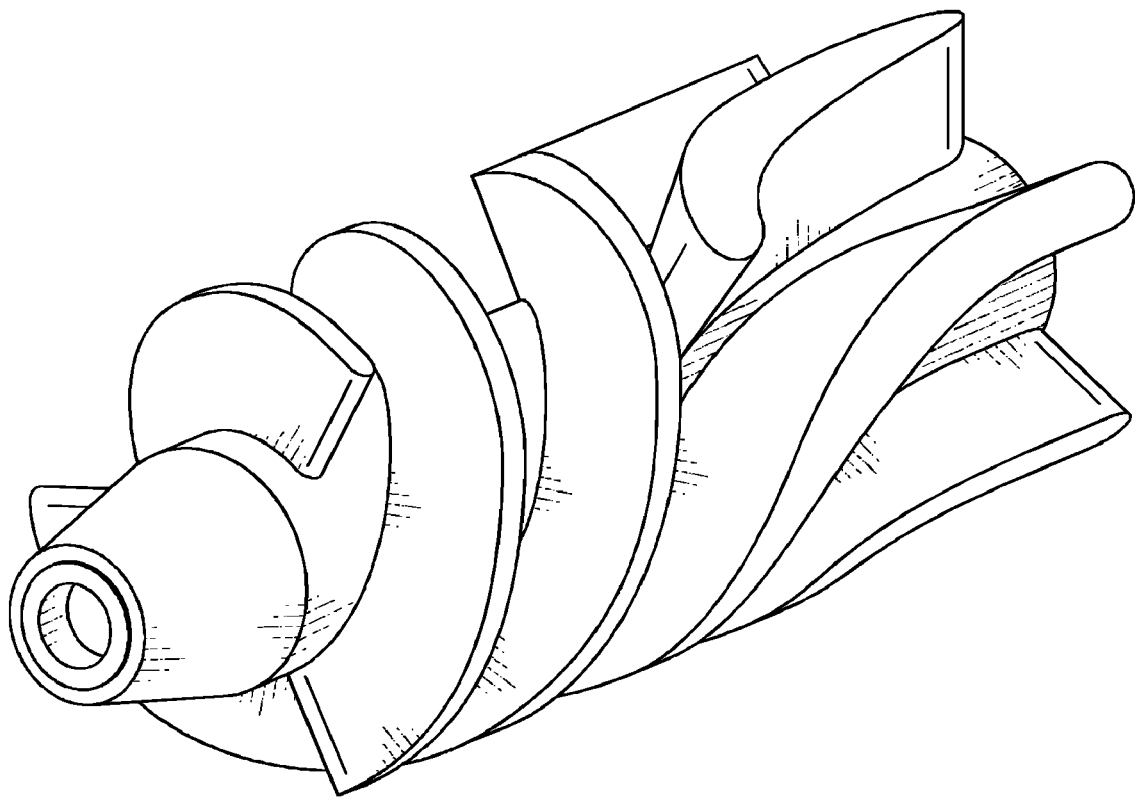
FIG. 5 illustrates an impeller with a bearing in the front hub section.

FIG. 5 shows the impeller with a bearing installed in the front hub section of the impeller.

Other and further embodiments utilizing one or more aspects of the inventions described above can be devised without departing from the spirit of Applicant's invention. Discussion of singular elements can include plural elements and vice-versa.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to fully protect all such modifications and improvements that come within the scope or range of equivalent of the following claims.

What is claimed is:

1. A blood pump comprising:
a flow straightener, the flow straightener including a flow straightener body with a plurality of blades extending outwardly from the body and a front shaft fixedly extending rearwardly from the body;
an impeller downstream of the flow straightener, rotatably supported by the shaft; and
a diffuser downstream of the impeller,
wherein the flow straightener is configured to minimize flow recirculation between the flow straightener and the impeller.

2. The blood pump from claim 1 wherein the impeller comprises a bearing on a front hub section.

3. The blood pump from claim 1 wherein the flow straightener body has a body contour which is shaped such that a rear section of the flow straightener body blends into the shaft and there is no axial gap between the flow straightener other than the ends of the blades and the impeller.

4. The blood pump from claim 1 wherein the flow straightener body has a body contour that blends into the shaft to minimize any axial gap between the flow straightener body and the impeller.

5. The blood pump from claim 1 wherein the flow straightener body has a continuous body contour that blends into the shaft to eliminate any axial gap between the flow straightener body and the impeller.

6. The blood pump from claim 1 wherein the flow straightener is configured to eliminate any flow recirculation between the flow straightener and the impeller.

7. A blood pump comprising:
a flow straightener having a body and a shaft;
an impeller downstream of the flow straightener having a bearing which accepts the shaft of the straightener; and
a diffuser downstream of the impeller,
wherein the flow straightener is configured to minimize any axial gap between the body and the shaft, and thereby minimize flow recirculation between the flow straightener and the impeller.

8. The blood pump from claim 7 flow straightener body has a body contour which is shaped such that the rear section of the flow straightener body blends into the shaft and there is no axial gap between the flow straightener other than the ends of the blades and the impeller.

9. The blood pump from claim 7 wherein the flow straightener body has a body contour that blends into the shaft to eliminate any axial gap between the flow straightener body and the impeller.

10. The blood pump from claim 7 wherein the flow straightener body has a continuous body contour to the shaft to eliminate any axial gap between the flow straightener body and the impeller.

11. The blood pump from claim 7 wherein the flow straightener is configured to eliminate any flow recirculation between the flow straightener and the impeller.

12. A blood pump comprising:
a flow straightener having a body, a plurality of blades extending axially from the body and a shaft extending rearwardly from the body;
an impeller downstream of the flow straightener; and
a diffuser downstream of the impeller,
wherein the body has a continuous body contour to the shaft eliminating any axial gap between the body and the shaft, and thereby minimize flow recirculation between the flow straightener and the impeller.

13. The blood pump from claim 12 wherein the flow straightener is configured to eliminate any flow recirculation between the flow straightener and the impeller.

14. The blood pump from claim 7, wherein the body and the shaft of the flow straighter are fixedly mounted and the impeller is rotatably supported by the shaft.

15. The blood pump from claim 12, wherein the body and the shaft of the flow straighter are fixedly mounted and the impeller is rotatably supported by the shaft.

* * * * *